(12) United States Patent
Jin et al.

(10) Patent No.: US 12,011,296 B2
(45) Date of Patent: Jun. 18, 2024

(54) SYSTEMS AND METHODS FOR IMPLANTING AN IMPLANTABLE CARDIAC MONITOR

(71) Applicant: Pacesetter, Inc., Sylmar, CA (US)

(72) Inventors: Li Jin, Cupertino, CA (US); Gene A. Bornzin, Simi Valley, CA (US); Zoltan Somogyi, Simi Valley, CA (US); Alex Soriano, Ventura, CA (US); Jake Singer, Santa Monica, CA (US); Tejpal Singh, Stevenson Ranch, CA (US); Wenbo Hou, Santa Clarita, CA (US); Julie Prillinger, Redwood City, CA (US); Armando M. Cappa, Granada Hills, CA (US); Mitch Goodman, Santa Clarita, CA (US); Tracee Eidenschink, Wayzata, MN (US)

(73) Assignee: Pacesetter, Inc., Sylmar, CA (US)

( * ) Notice: Subject to any disclaimer, the term of this patent is extended or adjusted under 35 U.S.C. 154(b) by 408 days.

(21) Appl. No.: 17/538,473

(22) Filed: Nov. 30, 2021

(65) Prior Publication Data
US 2022/0079523 A1    Mar. 17, 2022

Related U.S. Application Data

(63) Continuation of application No. 15/387,144, filed on Dec. 21, 2016, now abandoned.

(51) Int. Cl.
| | | |
|---|---|---|
| *A61M 25/01* | (2006.01) | |
| *A61B 5/00* | (2006.01) | |
| *A61B 5/361* | (2021.01) | |
| *A61M 37/00* | (2006.01) | |

(52) U.S. Cl.
CPC .............. *A61B 5/686* (2013.01); *A61B 5/361* (2021.01); *A61B 2560/063* (2013.01)

(58) Field of Classification Search
CPC ........ A61M 2005/1585; A61M 5/3287; A61M 25/0102; A61M 37/0069; A61M 31/007
See application file for complete search history.

(56) References Cited

U.S. PATENT DOCUMENTS

| | | |
|---|---|---|
| 4,646,755 A | 3/1987 | Kane |
| 4,900,304 A | 2/1990 | Fujioka et al. |
| 6,412,490 B1 | 7/2002 | Lee |
| 6,450,938 B1 | 9/2002 | Miller |
| 9,198,591 B2 | 12/2015 | Brockway et al. |
| 2003/0135153 A1 | 7/2003 | Hagenmeier |
| 2004/0010231 A1 | 1/2004 | Leonhardt et al. |

(Continued)

*Primary Examiner* — Joseph A Stoklosa
*Assistant Examiner* — Brian M Antiskay
(74) *Attorney, Agent, or Firm* — Dean D. Small; The Small Patent Law Group, LLC

(57) ABSTRACT

Systems and methods are provided for implanting an implantable cardiac monitor. An insertion system includes an implantable cardiac monitor (ICM). An insertion housing comprises a passage extending from a first end of the insertion housing to a second end of the insertion housing. The passage configured to receive the obturator and a receptacle in communication with the passage and an external environment. The receptacle configured to receive the ICM. An obturator is configured to move within the passage when the obturator is moved relative to the insertion housing. The obturator has a channel forming section at a distal end thereof and a motion limiter is provided on at least one of the shaft and the insertion housing.

14 Claims, 12 Drawing Sheets

(56) References Cited

U.S. PATENT DOCUMENTS

| | | |
|---|---|---|
| 2004/0054388 A1 | 3/2004 | Osypka |
| 2004/0172089 A1 | 9/2004 | Whitehurst et al. |
| 2007/0179388 A1 | 8/2007 | Larik et al. |
| 2008/0071246 A1 | 3/2008 | Nazzaro et al. |
| 2008/0269763 A1 | 10/2008 | Bonde et al. |
| 2010/0030227 A1 | 2/2010 | Kast et al. |
| 2010/0331868 A1 | 12/2010 | Bardy |
| 2011/0166448 A1 | 7/2011 | Jones et al. |
| 2013/0304078 A1 | 11/2013 | Issacs et al. |
| 2014/0276037 A1 | 9/2014 | Johnson et al. |
| 2014/0276928 A1 | 9/2014 | Vanderpool et al. |
| 2015/0151077 A1 | 6/2015 | Harrington |
| 2016/0128784 A1 | 5/2016 | Ahari |
| 2016/0175007 A1 | 6/2016 | Valbuena et al. |
| 2016/0296739 A1 | 10/2016 | Cleveland |

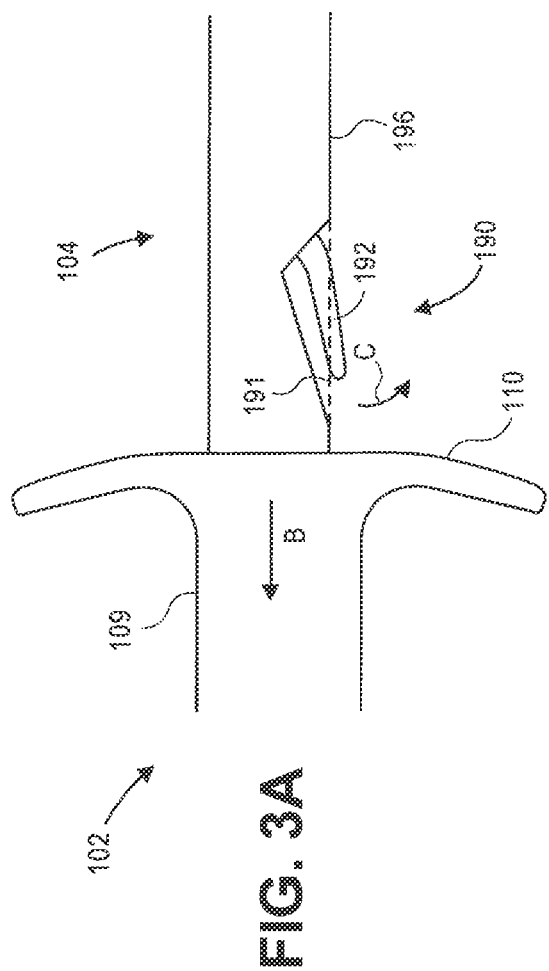
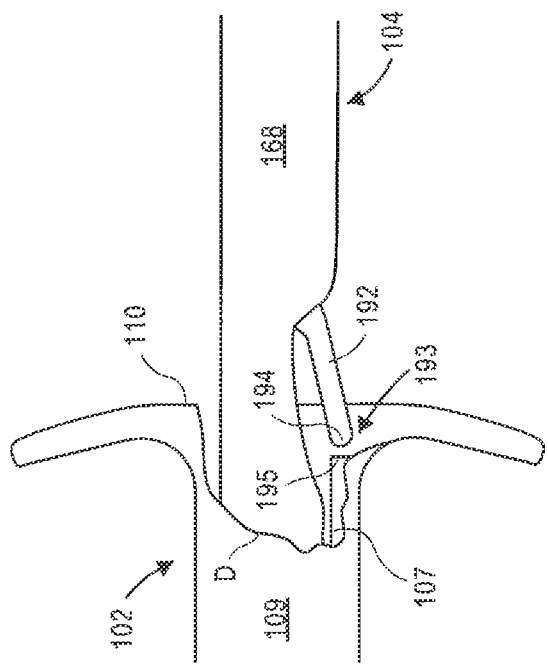

SYSTEMS AND METHODS FOR IMPLANTING AN IMPLANTABLE CARDIAC MONITOR

REFERENCE TO RELATED APPLICATIONS

The present application is a continuation application of, and claims priority to, U.S. Application Ser. No. 15/387,144, Titled "SYSTEMS AND METHODS FOR IMPLANTING AN IMPLANTABLE CARDIAC MONITOR" which was filed on Dec. 21, 2016, the complete subject matter of which is expressly incorporated herein by reference in its entirety.

FIELD OF THE DISCLOSURE

The present disclosure relates generally to implantable cardiac monitors (ICMs), and more particularly to systems and methods for implanting ICMs.

BACKGROUND

Implantable cardiac monitors (ICMs) are devices that may be implanted under a patient's skin to continuously monitor the patient's cardiac activity. An ICM may be programmed to detect and record cardiac information and episodes such as atrial/ventricular tachycardia, atrial fibrillation, bradycardia, asystole, etc. Triggers for detecting and recording an event (e.g., such a Tachy/Brady detection rate, a number of events, and/or a duration of asystole) may be programmed by a clinician. Alternatively, when the patient experiences symptoms, the patient may activate the detection and recording using an external patient activator. Diagnostics and recorded events may be downloaded by the clinician in-clinic using a programmer. Further, the data may also be transmitted to the clinician using a daily remote monitoring system.

As compared to external cardiac monitors, ICMs allow clinicians to monitor the patient's cardiac activity for an extended period of time, with an average longevity of up to 36 months. The information recorded by ICMs enables clinicians to determine if a patient complaining of symptoms has irregularities in their heart rhythm that cannot be confirmed in the clinic, particularly for transient and/or infrequent arrhythmias. The information can also aid the clinician in determining the best course of treatment for the patient (e.g., an addition or change of medication, a procedure such as cardioversion or ablation to restore a regular heart rhythm, and/or implantation of a pacemaker or implantable cardioverter defibrillator for long-term treatment of an irregular heart rhythm).

ICMs are generally small (e.g., 1.1-1.5 $cm^3$ in volume), and can be implanted using a small incision (e.g., 1 cm). Once inserted under the patient's skin, the ICM has a slim profile, mitigating patient concerns of comfort and aesthetics/body image. The ICM may be implanted in the patient's chest area near the sternum, and the implant procedure may take less than 2 minutes after application of a local topical anesthesia. Further, ICMs are diagnostic tools that do not deliver pacing or shock therapies to the patient, nor do they require leads to be implanted in the patient's heart.

At least one known method for implanting ICMs includes creating an incision, inserting a tool into the incision and rotating it to create a pocket under the skin, and inserting the ICM using a obturator system that pushes the device in and uses the tool as a guide. However, using at least some known insertion systems, the incision may be difficult to keep open during the procedure. Further, it may be difficult to maneuver the tool into the tissue to position the ICM. For patients with taut tissue, additional force may be required to insert the ICM, while for patients with loose tissue, the ICM may move after implant if a pocket created for the ICM is large. Moreover, in at least some known insertion systems, it may be difficult to push the ICM, which typically has rounded edges, into tissue. Finally, once the ICM is implanted, at least some known insertion systems are difficult to remove from the patient.

Furthermore, ICM utilize QRS detection to determine R-R intervals utilized in connection with monitoring cardiac activity. However, ICM systems may exhibit difficulties in detecting the R-R interval when the QRS complex has low amplitude (e.g., less than approximately 0.2 mV). As one example, approximately 10% of implants may experience low amplitude QRS complexes, particularly in connection with patients who have larger body mass indices. Patients with an overly large body mass index may have the ICM implanted in superficial adipose tissue that is far removed from the heart.

Given the ease at which ICMs may be implanted, some physicians may regard the implant of an ICM as a minor event and may not consider whether the implant location and orientation will yield a QRS complex with sufficient amplitude. Only later, after the implant has healed in place, is it determined that the detected signals are too small. Thereafter, the ICM is removed and re-implanted which introduces an unnecessary procedure that is inconvenient, expensive and has at least some risk of infection. Other physicians may use external electrodes to map an ideal location and orientation on the surface of the patient's skin prior to ICM implant; however, this adds significant time to the procedure and may not yield acceptable post-implant QRS amplitudes, which are subsequently measured subcutaneously.

In some ICMs, P-waves are captured from an EKG signal in order to provide evidence of sinus rhythm. An absence of P-waves is used to support a determination as to whether a patient is experiencing atrial fibrillation (AF). In subsequent analysis of the information collected by an ICM, when determining whether a patient is experiencing AF, it is desirable for clinicians to view P-wave activity in the stored data in order to facilitate diagnosis. However, discerning P-waves may be challenging given that P-waves are relatively small features as compared to R-waves (approximately 20 to 25% of the amplitude of an R-wave). While ensemble averaging between multiple cardiac cycles may be utilized in an attempt to enhance P-waves, ensemble averaging utilizes additional processing power and reduces the ICM longevity.

A need remains for systems and methods that address the problems described above and that are apparent from the description herein.

BRIEF SUMMARY OF THE DISCLOSURE

In accordance with embodiments herein, an insertion system is provided. The system comprises an implantable cardiac monitor (ICM). An insertion housing comprises a passage extending from a first end of the insertion housing to a second end of the insertion housing. The passage configured to receive the obturator and a receptacle in communication with the passage and an external environment. The receptacle configured to receive the ICM. An obturator is configured to move within the passage when the obturator is moved relative to the insertion housing. The obturator has a channel forming section at a distal end thereof and a motion limiter is provided on at least one of the shaft and the insertion housing.

Optionally, the second range represents an ICM final implant path. The motion limiter may define an end of the ICM final implant path. A distal end of the obturator may be positioned substantially flush with the second end of the insertion housing when reaching the end of the ICM final implant path. The first range may represent a pocket formation path. The motion limiter may include a latch arm located along a side of a shaft of the obturator and may be at least one recessed region in the passage. The latch arm may extend laterally outward from the side into the at least one recessed region when the obturator moves to an end of the pocket formation path and when the obturator moves to an end of the ICM final implant path. The motion limiter may include at least one latch and at least one recessed region provided on the obturator and insertion housing.

Optionally, the obturator may include a channel forming section that may be provided at a distal end of the obturator. The channel forming section may have a cross-section and may be sized and dimensioned similar to a cross-section, size, and dimension of the ICM. The insertion housing may include a blunt dissection barrel provided at the second end. The blunt dissection barrel may have a tapered edge that may be configured to be utilized during a blunt dissection stabbing action to form and hold-open an initial channel under patient tissue. The blunt dissection barrel may have a length that is shorter than a length of the ICM. The length of the blunt dissection barrel may be no more than one third of a length of the ICM. The system may further comprise a pullback stop feature that may include a pin and groove provided on the insertion housing and obturator. The pin may ride within the groove when the obturator is moved relative to the insertion housing. The pin and groove may define a retracted range limit to which the obturator is removed from the insertion housing such that the obturator is not accidentally removed from the insertion housing.

In accordance with embodiments herein, a method is provided for operating an insertion system. The method comprises providing an obturator in a passage in an insertion housing such that the obturator extends from a first end of the insertion housing to a second end of the insertion housing. The method installs an implantable cardiac monitor (ICM) into a receptacle of the insertion housing. The receptacle is in communication with the tube of the insertion housing. The obturator is configured to move along a first range until the channel forming section extends a predetermined distance from the second end of the insertion housing. The predetermined distance is defined by the motion limiter. The obturator is configured to move along a second range in which the channel forming section forces the ICM from the second end of the insertion housing. Optionally, the ICM may be pre-installed into the insertion tool before the implant procedure begins.

Optionally, the method further comprises initially positioning the obturator and insertion housing in a blunt dissection state. A blunt dissection barrel at the second end of the insertion housing is inserted in an incision to a desired depth, moving the obturator along a range of motion corresponding to an ICM pocket formation path until reaching a fully extended position corresponding to an ICM pocket formation state. Optionally, the method may apply force to a handle of the obturator to direct a channel forming section at the distal end of the obturator to extend from the second end of the insertion housing in order to form an ICM pocket.

Optionally, once the ICM pocket is formed, pulling back on the obturator until the channel forming section of the obturator is positioned behind the receptacle of the insertion housing in order to permit the ICM to move into the insertion passage (path between the first and second ends of the insertion housing). The method may apply force to the handle of the obturator to direct the distal end of the obturator to discharge the ICM from the second end of the insertion housing into the ICM pocket. The method may move the obturator relative to the insertion housing until reaching a motion limiter, the motion limiter defining at least one of an end for a pocket forming state or an ICM final implant state for the obturator and insertion housing.

In accordance with embodiments herein, an insertion system is provided. The system comprises an implantable cardiac monitor (ICM) including first and second ICM electrodes configured to be utilized in connection with sensing physiologic signals, the first and second ICM electrodes separated by an electrode spacing. A medical instrument is provided. The medical instrument comprises a shaft with a channel preparation element that is configured to be inserted subcutaneously into an ICM channel region and first and second instrument electrodes provided on the channel preparation element and are configured to sense physiologic signals during an ICM implant process prior to device insertion. The first and second instrument electrodes are separated by the electrode spacing.

Optionally, the channel preparation element may represent a needle (e.g., a lumen built-in to the obturator) having a distal end and a proximal end. The first and second instrument electrodes may be provided on the needle at the distal and proximal ends, respectively. Conductors may be coupled to the first and second instrument electrodes and may extend along the needle. The conductors may have proximal ends with contacts configured to be electrically coupled to at least one of the ICM or an external device.

Optionally, the medical instrument may further comprise a syringe coupled to the proximal end of the needle. The medical instrument may further comprise a probe body that includes a receptacle configured to receive the ICM. The receptacle may include first and second contacts spaced apart from one another and may be positioned to align with the first and second ICM electrodes. The first and second contacts may be electrically coupled to the first and second instrument electrodes and may be configured to convey physiologic signals sensed by the first and second instrument electrodes to the ICM. The channel preparation element may represent a needle with a distal end and a proximal end. The proximal end may be coupled to the probe body. The first and second instrument electrodes may be provided on the distal and proximal ends, respectively, of the needle.

Optionally, the medical instrument may comprise an insertion housing. The insertion housing may comprise a passage extending from a first end of the insertion housing to a second end of the insertion housing. The passage may be configured to receive the obturator. The insertion housing may further comprise a receptacle in communication with the passage and an external environment. The receptacle may be configured to receive the ICM. The shaft may represent an obturator configured to move within the passage when the obturator is moved relative to the insertion housing. The channel preparation element may represent a channel forming section at a distal end of the obturator. The first and second instrument electrodes may be provided on the channel forming section and may be configured to collect the physiologic signals when the channel forming section is extended to a pocket formation state subcutaneously in the ICM channel region.

In accordance with embodiments herein a method is provided for mapping an implant location and orientation (vertical, diagonal, horizontal for an implantable cardiac monitoring (ICM) device. The method comprises inserting a channel preparation element of a medical instrument subcutaneously into an ICM candidate location. The method senses physiologic signals at instrument electrodes located along the channel preparation element, utilizes one or more processors to analyze a characteristic of interest from the physiologic signals relative to a signal criterion, and designates the ICM candidate location as a final ICM implant location based on the analysis of the characteristic of interest.

Optionally, the method may further comprise maintaining the channel preparation element at an ICM candidate position and orientation while sensing the physiologic signals. The method may record the physiologic signals at the ICM. The ICM may analyze the characteristic of interest from the physiologic signals. The method may record the physiologic signals to the ICM. The ICM may designate whether the ICM candidate location qualifies as a final ICM implant location.

Optionally, the method further comprises conveying the physiologic signals to the ICM. The ICM may convey the physiologic signals to an external device. The external monitoring device may perform the analyzing operation. The channel preparation element may represent a needle having a distal end and a proximal end. The instrument electrodes may be provided on the needle at the distal and proximal ends. The method may comprise conveying the physiologic signals from the instrument electrodes to at least one of the ICM or an external device. The medical instrument may comprise a probe body. The method may insert the ICM into a receptacle provided in the probe body where ICM electrodes on the ICM engage contacts within the receptacle. The ICM may record the physiologic signals sensed by the instrument electrodes.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 3A illustrates a portion of the insertion housing and obturator when the obturator is at an ICM intermediate implant state in accordance with embodiments herein.

FIG. 3B illustrates a portion of the insertion housing and obturator when the obturator is inserted to an ICM final implant state in accordance with embodiments herein.

Corresponding reference characters indicate corresponding parts throughout the several views of the drawings.

DETAILED DESCRIPTION OF THE DISCLOSURE

The present disclosure provides systems and methods for implanting an implantable cardiac monitor (ICM). An insertion system includes an implantable cardiac monitor, an obturator and an insertion housing. The insertion housing includes a barrel extending from a first end of the insertion housing to a second end of the insertion housing, the barrel configured to receive the ICM and the obturator. Embodiments herein include one or more of various unique features described hereafter.

Figure 1A:
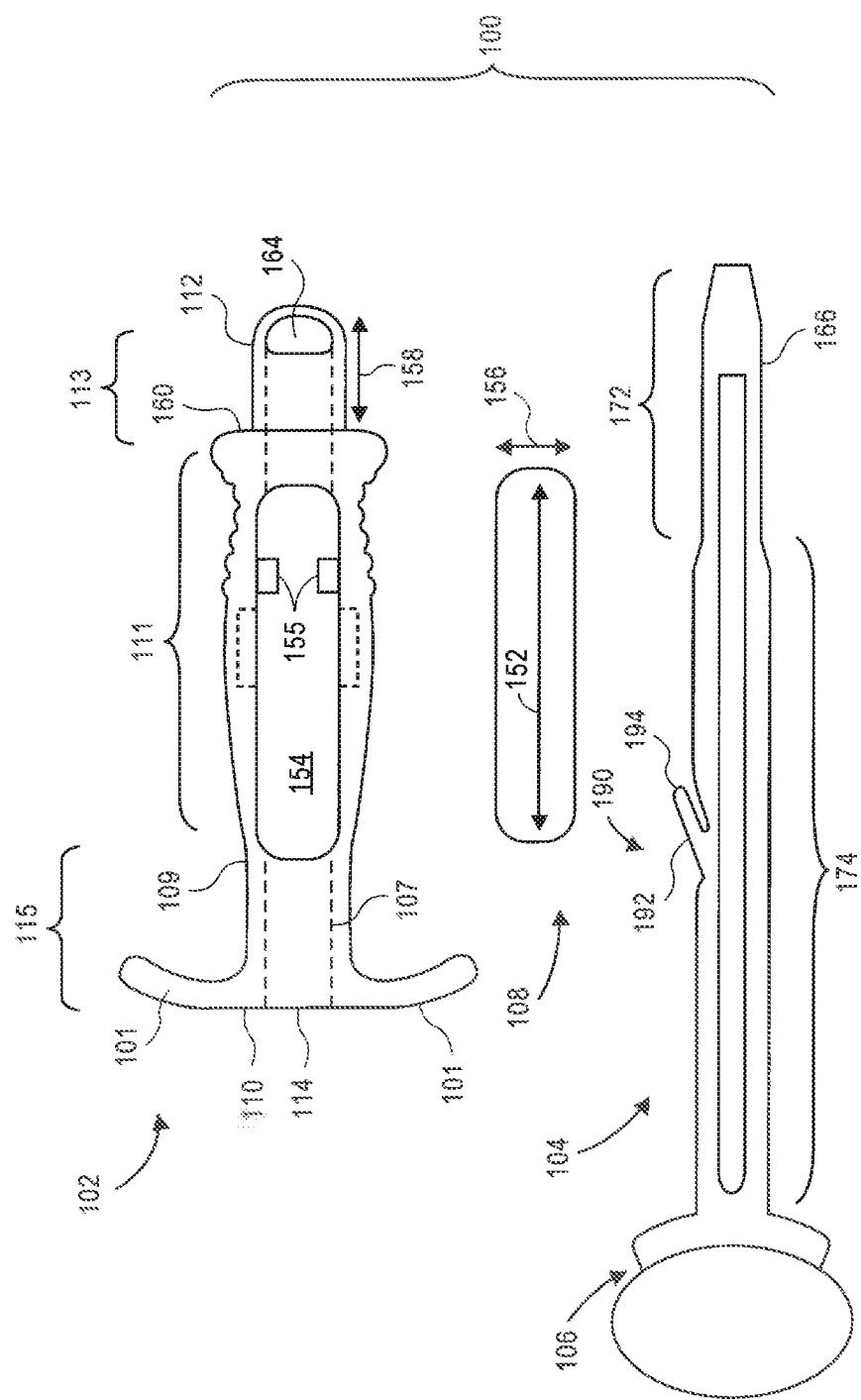
FIG. 1A is a schematic view of one embodiment of an implantable cardiac monitor (ICM) insertion system in accordance with embodiments herein.
Figure 1B:
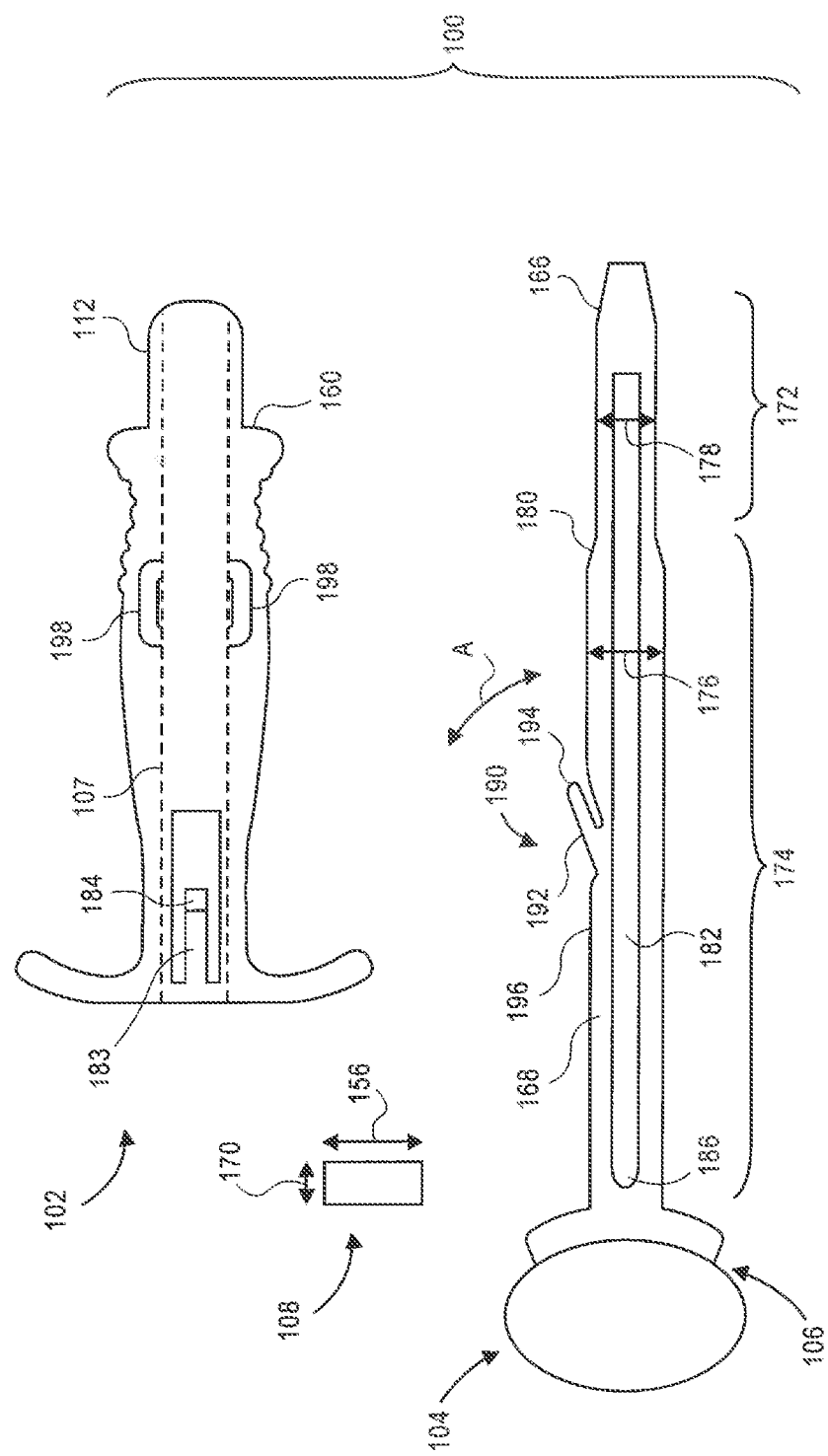
FIG. 1B illustrates the insertion housing and obturator from an opposite side to the view shown in FIG. 1A in accordance with embodiments herein.
Figure 4A:
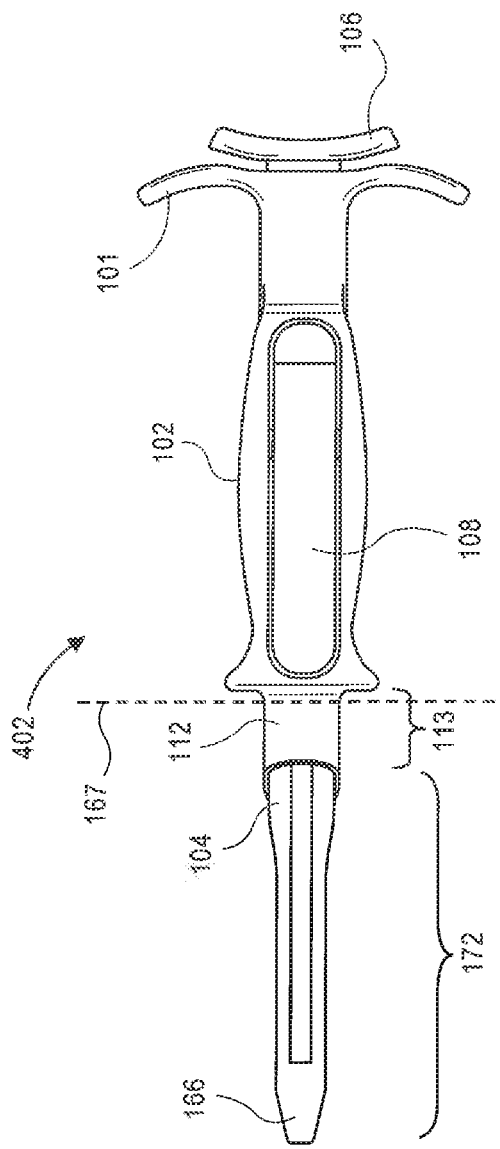
FIG. 4A illustrates a pocket formation state, at which the obturator is extended through the insertion housing in accordance with embodiments herein.
Figure 4B:
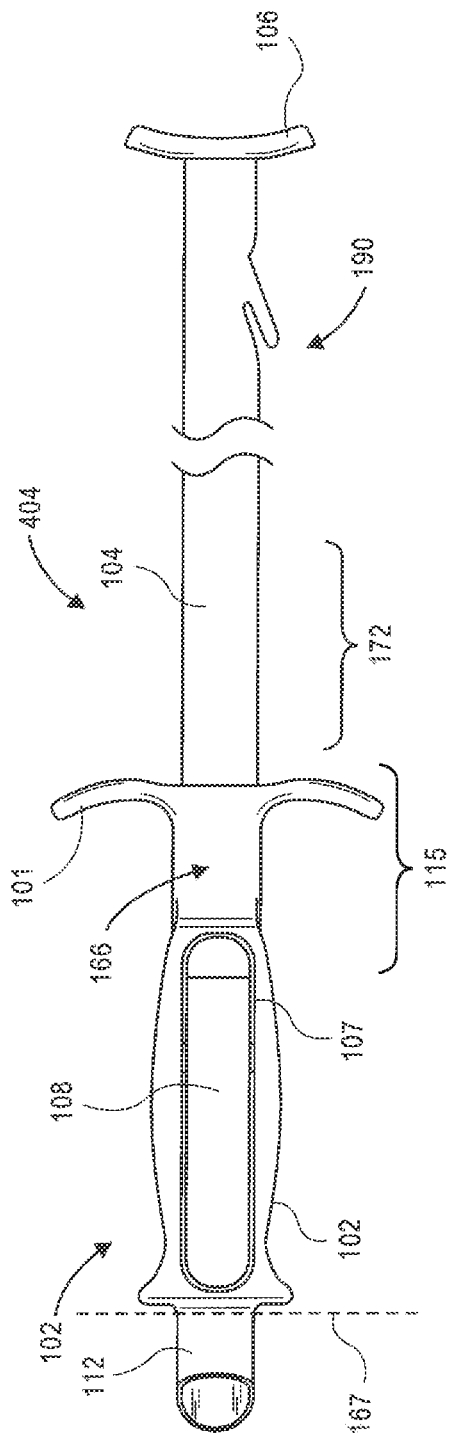
FIG. 4B illustrates an ICM loading state, at which the obturator is substantially withdrawn from the insertion housing, in accordance with embodiments herein.
Figure 4C:
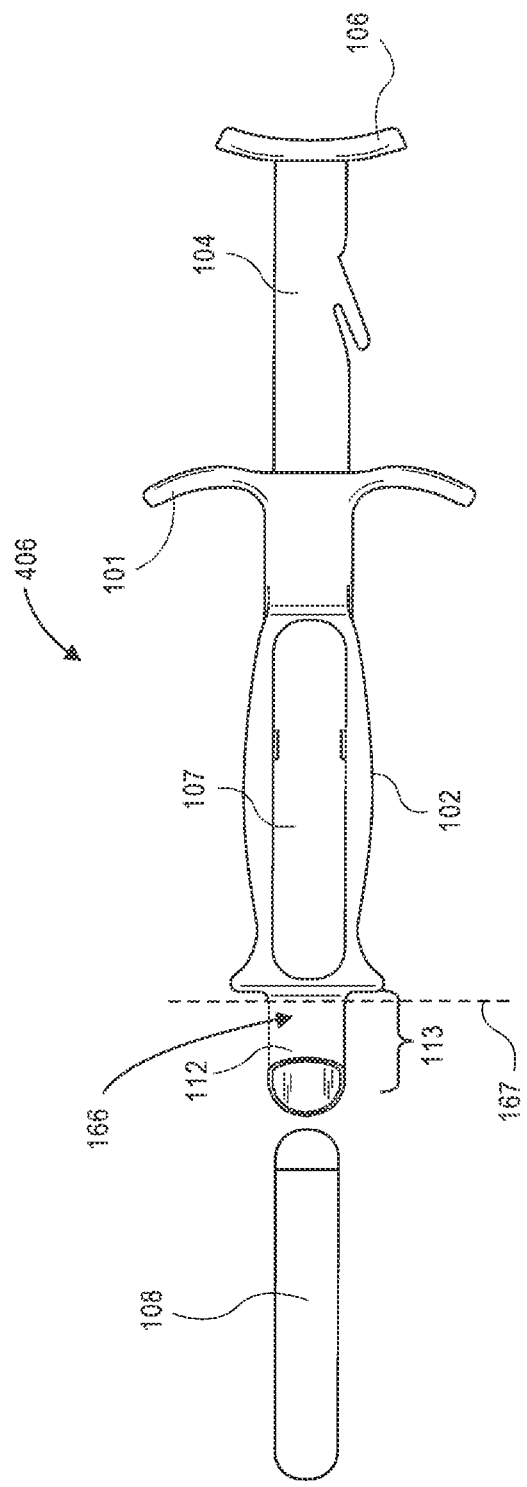
FIG. 4C illustrates an ICM final implant state in accordance with embodiments herein.

Referring now to the drawings and in particular to FIGS. 1A and 1B, an ICM insertion system is indicated generally at 100. Components of insertion system 100 include an insertion housing 102, an obturator 104 and an ICM 108. In FIGS. 1A and 1B, the components of insertion system 100 are shown separate from one another (i.e., in a disassembled state). In FIGS. 4A-4C, the components of insertion system 100 are shown in an assembled state.

Insertion housing 102 includes a barrel 109, with a passage there through, that extends from a first/proximal end 110 to a second/distal end 112. In this embodiment, barrel 109 has a substantially rectangular cross section. Alternatively, barrel 109 may have any shape that enables insertion system 100 to function as described herein.

The passage 107 extends along a length of the barrel 109 of the insertion housing 102. The passage 107 has a cross-section that substantially conforms to the cross-section of the ICM 108. The passage 107 includes inner dimensions (width and thickness) that are similar to, but slightly larger than, the outer dimensions (width and thickness) of the ICM 108, such that ICM 108 can be positioned within, and movable along, the passage 107. The first end 110 includes an opening 114 to facilitate inserting the obturator 104 into insertion housing 102. The distal end 112 includes a discharge opening 164, from which the ICM 108 is discharged into a channel under a patient's tissue when the ICM 108 is ejected by the distal end 166 of the obturator 104. Example shapes for the distal end 112 are discussed below in more detail in connection with FIG. 2A.

A tip is formed at the distal end 166 of the obturator 104. The tip is shaped and dimensioned to perform blunt dissection in subcutaneous tissue of the patient as the obturator 104 is extended from the distal end 112 of the insertion housing 102. In the illustrated embodiment, the tip has a tapered conical shape. Alternatively, the tip may have any shape that enables obturator 104 to function as described herein. For example, the tip may have an oval shape, a duckbill shape, a wedge shape, a hook shape, and/or any other suitable shape. The obturator 104 may be fabricated from, for example, polycarbonate, polysulfone, or another similarly resilient material. In some embodiments, for comfort and/or usability, the handle 106 of the obturator 104 or ribs 103 is formed from a softer material (e.g., silicone).

The barrel 109 includes a central receptacle section 111, joined at one end to a blunt dissection barrel 113 and at another end to a proximal section 115, all formed integral with one another. The proximal segment 115 includes a pair of wings 101 that extend in opposite directions from the barrel 109. They wings 101 are configured to be held between two fingers, such as the index finger and middle while the user's thumb or palm of the hand press on the handle 106. For example, the wings 101 may be concave similar to a syringe to facilitate holding the tool similar to a syringe. The blunt dissection barrel 113 is shaped and dimensioned to be utilized during a blunt dissection stabbing action to form an initial channel under the skin at an incision location. The proximal section 115 and receptacle session 111 include a peripheral contour that facilitates gripping by a user during operation. The receptacle section 111 includes an ICM reception cavity 154 therein. The receptacle cavity 154 is configured to receive the ICM 108 during an implant process. The ICM reception cavity 154 is shaped and dimensioned to conform to a shape of the ICM 108, and as such has a length and width substantially similar to, but slightly larger than the length 152 and width 156 of the ICM 108. For example, the receptacle cavity 154 may have a length of approximately 40-50 mm and a width of 5-10 m. Optionally, alternative dimensions may be utilized based on the size of the ICM 108. The receptacle section 111 includes a length that is at least slightly longer than the length 152 of the ICM 108. The reception cavity 154 includes one or more detents 155 extending inward from a perimeter thereof. The detents 155 may be aligned with one another or misaligned relative to one another. The detents 155 are configured to resist removal of the ICM 108 once the ICM 108 is inserted into the reception cavity 154, such that detents 155 prevents the ICM 108 from inadvertently falling out of the reception cavity 154 and from being dropped onto a nonsterile surface such as the floor. The reception cavity 154 is located directly above and in communication with a portion of the passage 107 that passes through the receptacle section 111. The reception cavity 154 has a depth that is sufficient to hold the ICM 108 while the obturator 104 is located in the passage 107 directly below the ICM 108.

The blunt dissection barrel 113 extends from the receptacle section 111 toward the distal end 112. The blunt dissection barrel 113 is formed with a length 158 that is short in relation to the overall length 152 of the ICM 108. By way of example only, a length 158 of the blunt dissection barrel 113 may be approximately ¼ or ⅓ of the length 152 of the ICM 108. Alternatively, the blunt dissection barrel 113 may be longer or shorter. In the present embodiment, the blunt dissection barrel 113 is formed relatively short in order to simplify certain types of insertion processes. In addition, by utilizing a short blunt dissection barrel 113, the system 100 avoids forming an unduly large channel in which the ICM 108 may ultimately shift. During the implant process, the blunt dissection barrel 113 is inserted (e.g., through a blunt dissection stabbing action) into an incision until the skin abuts against a leading edge 160 of the receptacle section 111.

Figure 2A:
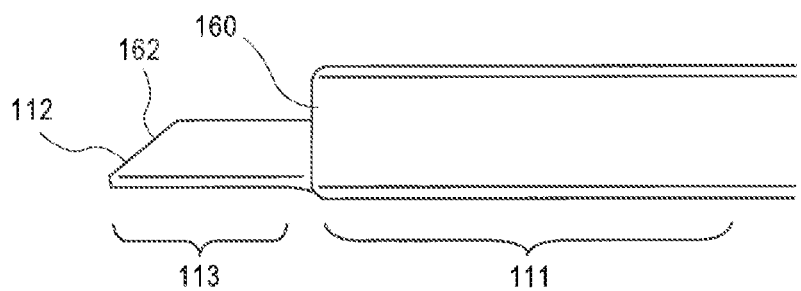
FIG. 2A illustrates a side view of the blunt dissection barrel formed in accordance with an embodiment herein.

FIG. 2A illustrates a side view of the blunt dissection barrel 113 formed in accordance with an embodiment herein. As shown in FIG. 2A, the distal end 112 of the blunt dissection barrel 113 includes a tapered edge 162. The tapered edge 162 tapers relative to a side profile of the blunt dissection barrel 113. Optionally, the tapered edge 162 may be oriented to taper in alternative directions. Optionally, the tapered edge 162 can also have different contours, such as curved profile, as a means to facilitate gradual introduction of the barrel through the incision site to minimize trauma to the tissue. FIG. 2A also illustrates a step up in the height at the leading edge 160 at the intersection between the blunt dissection barrel 113 and the receptacle section 111. During an implant operation, the blunt dissection barrel 113 is inserted until skin at the point of incision abuts against the leading edge 160.

FIG. 1B illustrates the insertion housing 102 and obturator 104 from an opposite side to the view shown in FIG. 1A. FIG. 1B also illustrates an end view of an ICM 108. The ICM 108 includes a width 156 and thickness 170. By way of example, the ICM 108 may have a length of approximately 40-50 mm, a width of 5-10 m, and a thickness of 2-5 mm. The foregoing dimensions are merely an example, and other shapes and sizes may be utilized. In the present example, the ICM 108 has a rectangular cross-section with rounded edges. Optionally, the ICM 108 may have alternative cross-sections (e.g., square, tubular, polygon shaped, oval shaped and the like).

The obturator 104 includes an elongated shaft 168 that is elongated to extend from the handle 106 to a distal end 166. The shaft 168 may be shaped with various cross-sections. For example, the shaft 168 may be shaped with a rectangular cross-section that is sized and dimensioned to be similar to the rectangular cross-section of the ICM 108. The shaft 168 includes a beveled shape at the distal end 166, where the beveled shape joins a channel forming section 172. The channel forming section 172 joins a main body section 174 that extends along a substantial majority of the shaft 168 to the handle 106. The main body section 174 has a lateral width 176 that is greater than a lateral width 178 of the channel forming section 172. A smooth taper 180 is provided at the transition point between the main body and channel forming sections 174 and 172. By way of example, it may be desirable to provide the channel forming section 172 with a smaller cross-sectional envelope as compared to the cross-sectional envelope of the ICM 108, to facilitate the creation of a pocket with a desired size into which the ICM 108 is ultimately to be implanted. For example, the channel forming section 172 may have a slightly smaller width and thickness (as viewed in the cross-section), as compared to the width and thickness of the ICM in order that the ICM 108 will fit snugly into the pocket when inserted and avoid undue risk of shifting within the pocket.

The insertion housing 102 and obturator 104 include one or more pullback stop features that are configured to limit an extent to which the obturator 104 is retracted from the insertion housing 102 during a pullback operation.

Figure 2B:
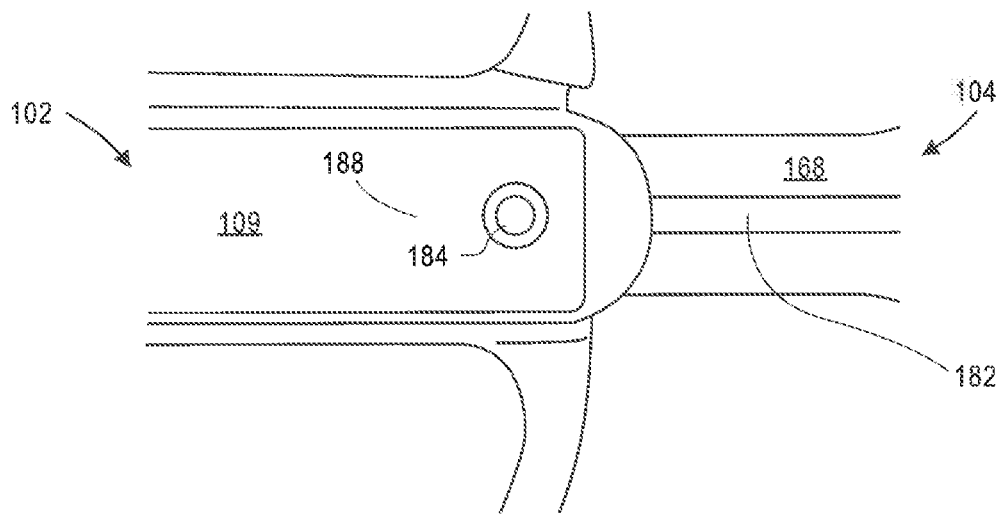
FIG. 2B illustrates a top plan view of a portion of the insertion housing and obturator joined to one another to better illustrate the pullback stop feature in accordance with embodiments herein.

FIG. 2B illustrates a top plan view of a portion of the insertion housing 102 and obturator 104 joined to one another to better illustrate the pullback stop feature. In the embodiment of FIGS. 1B and 2B, the pullback stop feature include a groove 182 that is provided along one or both sides of the shaft 168 of the obturator 104. The pullback stop feature also includes a pin 184 provided on a lever arm 183 formed with the barrel 109 of the insertion housing 102. The pin 184 extends inward into the passage 107 and is configured to align with the groove 182. The pin 184 rides within the groove 182 when the obturator 104 is linearly slid or moved relative to the insertion housing 102 within the passage 107. The arm 183 is flexible and biased inward toward the passage 107 to maintain the pin 184 engaged with the groove 182. The arm 183 may be flexed outward during assembly to permit the obturator 104 to be initially loaded into the passage 107. The groove 182 includes a retracted range limit 188. Optionally, the pin 184 may be molded as one solid piece with the lever arm 183.

The retracted range limit 188 is positioned at a point along a side of the obturator 104, such that the obturator 104 is able to be pulled back sufficiently that the distal end 166 clears the receptacle section 154, thereby allowing the ICM 108 to drop from the receptacle 154 into the passage 107. The pin 184 engages at least the retracted range limit 188 in order to prevent the obturator 104 from being entirely removed from the insertion housing 102. The pullback stop feature facilitates an implant process to become smoother as the user need not know when the pullback operation is completed, thereby removing uncertainty. The pullback stop feature also prevents the obturator 104 from inadvertently falling out of the barrel 109 and from being dropped onto a nonsterile surface such as the floor.

The insertion housing 102 and obturator 104 also include a forward motion limiter 190 (FIGS. 2C, 3A and 3B) that is configured to permit and limit forward movement of the obturator 104 within the barrel 109 over different ranges of motion during different stages of the ICM insertion process. During the pocket formation stage, the motion limiter 190 is moved over a first range to a first position, where the motion limiter 190 limits an amount to which the channel forming section 172 on the obturator 104 extends beyond the distal end 112 of the insertion housing 102. Accordingly, the motion limiter 190 defines a distance (channel formation range of motion) by which the channel forming section 172 extends from the distal end 112. Optionally, the motion limiter 190 may be removed and instead, the handle 106 may be configured to hit proximal end 110 to define the distance corresponding to the channel formation range of motion. During an ICM final implant state, the motion limiter 190 is moved over a second range to a second position, where the motion limiter 190 maintains the channel forming section 172 within the barrel 109 of the insertion housing 102. During the ICM final implant state, the motion limiter 190 prevents the channel forming section 172 from being discharged from the distal end 112. The motion limiter 190 is configured to prevent the user from pushing the ICM 108 deeper than the desired relative to the end of the blunt dissection channel (defined by the blunt dissection barrel 113).

Figure 2C:
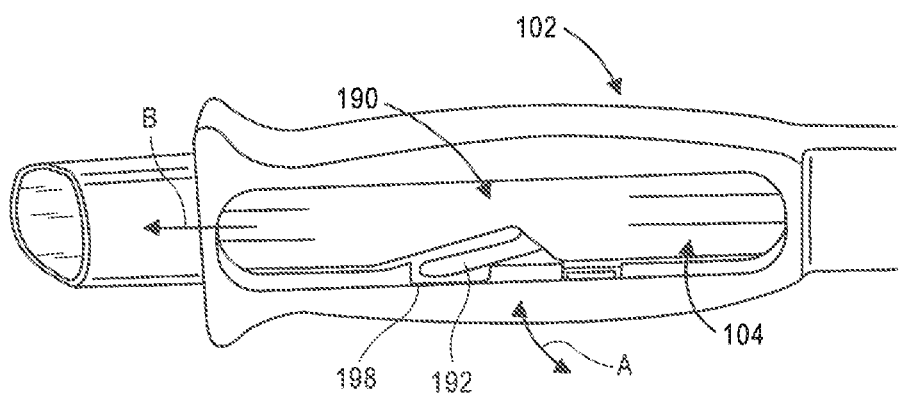
FIG. 2C illustrates a top plan view of a portion of the insertion housing and obturator to show the motion limiter when in the first position in accordance with embodiments herein.

FIG. 2C illustrates a top plane view of a portion of the insertion housing 102 and obturator 104 to show the motion limiter 190 when in the first position. With reference to FIGS. 1B and 2C, the motion limiter 190 is provided on at least one of the shafts 168 and/or the interior wall of the passage 107 in the insertion housing 102. The motion limiter 190 includes a latch arm 192 that extends laterally outward from a side of the shaft 168.

The latch arm 192 includes a distal tip 194 that, when in a relaxed unbiased position, extends laterally beyond a lateral envelope defined by the side 196 of the shaft 168. The latch arm 192 is configured to be deflected inward and outward (toward and away from the shaft 168) along directions denoted by arrow A. When deflected inward (i.e. pressed in intentionally by the finger of the user), the latch arm 192 moves to a position within a side envelope of the side 196, allowing obturator 104 to be repositioned along passage 107 of the insertion housing 102.

The motion limiter 190 also includes a recessed region 198 that is provided at a select point along the interior wall of the passage 107. The insertion housing 102 includes one or more recessed regions 198 provided along one or both sides of the passage 107. The lever arm 192 slides along the interior wall of the passage 107 until deflecting outward into one of the recessed region 198. FIG. 2C illustrates the latch arm 192 engaged within the recessed region 198. When the obturator 104 is fully inserted into the barrel 107, the latch arm 192 to flex laterally into the recessed region 198. The distal tip 194 of the lever arm 192 engages a wall of the recessed region 198 to prevent further forward movement (in the direction of arrow B) of the obturator 104, relative to the insertion housing 102. The recessed region 198 is positioned along the passage 107 a predetermined distance from the distal end 112 such that, when the latch arm 192 engages the recessed region 198, a predetermined length of the obturator extends from the distal end 112. In the present example, the recessed region 198 is positioned along the passage 107 such that the channel forming section 172 of the obturator 104 extends beyond the distal end 112 when the latch arm 192 engages the recessed region 198.

Optionally, the range of forward movement may be limited by the handle 106 of the obturator when stopped against the insertion housing 102.

The position of the latch arm 192 along the shaft 168, and/or the recesses region 198 along the passage 107 may be changed to adjust an amount of the obturator 104 that extends beyond the distal end 112 of the insertion housing 102. Optionally, the latch arm 192 may be located on the wall of the passage 107 and the recessed region 198 located on the shaft 168. Optionally, alternative motion limiting structures may be used in place of, or in addition to, the latch arm 192 and recessed region 198.

In addition, the cooperation between the recessed region 198 and the latch arm 192 afford a secondary purpose, namely to allow the latch arm 192 to assume a relaxed unbiased position while the obturator is fully inserted into the insertion housing 102 during storage and shipment. By allowing the latch arm 192 to maintain a relaxed position, without experiencing lateral loading during storage, embodiments herein avoid "creep" (also referred to as loss of lateral force) of the latch arm 192 into a deformed condition. When the latch arm 192 loses the lateral force or creeps, the latch arm 192 no longer engages the recessed region 198 and at least partially inhibits the operation of the motion limiter 190. When the latch arm 192 is not within the recessed region 198, the latch arm 192 exhibits a lateral friction force on the wall of the passage 107. The lateral friction force facilitates maintaining the obturator 104 in any given position relative to the insertion housing 102.

Optionally, a knob or other ergonomically appealing feature may be provided on the handle 106. For example, a knob may be added to the handle 106 in order that a user may hold the insertion barrel 109 between a thumb and forefinger while palming the obturator handle. The foregoing arrangement enables the user to maintain the obturator 104 in a fully inserted position in the barrel 109 during the blunt dissection action.

FIG. 3A illustrates a portion of the insertion housing 102 and obturator 108 when the obturator 104 is at an ICM intermediate implant state. FIG. 3B illustrates a portion of the insertion housing 102 and obturator 104 when the obturator 104 is inserted to an ICM final implant state. FIG. 3B also illustrates a portion of the barrel 109 cut out (along line D) to illustrate internal features within the insertion housing 102 at the proximal end 110.

In the position illustrated in FIG. 3A, the latch arm 192 is entirely removed from the proximal end 110 of the barrel 109. When entirely removed, the latch arm 192 flexes laterally outward in the direction of arrow C until extending beyond a lateral envelope 191 defined by the side 196. The lateral envelope 191 extends along the side 196. The obturator 104 is inserted into the insertion housing 102 in the direction of arrow B until reaching the position illustrated in FIG. 3B.

In the position illustrated in FIG. 3B, the latch arm 192 is received within the proximal end 110 of the insertion housing 102. A proximal recessed region 193 is provided at the proximal end 110. The proximal recessed region 193 is terminated at a ledge 195 that is located at a beginning of the passage 107. When the obturator is inserted to the ICM final implant state, the distal tip 194 of the latch arm 192 engages the ledge 195 to prevent further insertion of the shaft 168. When the latch arm 192 engages the ledge 195, the user recognizes that the distal end 166 (FIG. 1A) of the obturator 104 is proximate to the distal end 112 of the insertion housing 102 and has fully discharged the ICM 108. The ledge 195 is formed in the recessed region 193 to catch the latch arm 192. By providing the recessed region 193, the system 100 prevents the latch arm 192 from flaring further outward in the event pressure is applied to the obturator 104. Additionally, ledge 195 may be angled by design to deflect latch arm 192 outward and harder into recess 193 such that if the user forcefully advanced the obturator 104 in direction B, there would be increased force locking the latch arm 192 into recess 193, rather than latch arm 192 "slipping" into passage 107. Additionally, the angle of ledge 195 and the angle of latch arm 192 may be designed to take advantage of the column strength of latch arm 192 when pressed in recess 193

Optionally, the recessed region 193 and ledge 195 may be formed as a notch that receives the tip 194 of the latch arm 192.

The foregoing example describes a motion limiter that includes a latch arm that extends laterally outward from a side of the shaft of the obturator 104 when the obturator moves to an end of the pocket formation path and when the obturator moves to an end of the ICM final implant path. In the foregoing example, the motion limiter includes a latch arm and at least two recessed regions 198 and 193. Optionally, additional latch arms may be utilized and one or more than two recessed regions may be utilized to form the motion limiter. As a further option, a first latch arm may be utilized to define the end of the pocket formation path, while a second latch arm is utilized to define an end of the ICM final implant path. Optionally, the latch arm or arms may be provided on the interior wall of the passage 107 and oriented to deflect into the passage 107, while recessed regions are provided along the side of the shaft 168 of the obturator 104.

The insertion housing 102 may be relatively firm to maintain its shape as insertion housing 102 is inserted into the incision. Accordingly, insertion housing 102 and obturator 104 may be fabricated from, for example, polycarbonate, polysulfone, or another similarly resilient material. The obturator handle 106 may be fabricated from, for example, polycarbonate or silicone. Various ergonomic features may be utilized such as using more grip-friendly materials. Additionally or alternatively, as another grip-friendly feature, the wings may be formed on the insertion housing and ribs may be formed on the housing, all or a portion of which may be made with a urethane or other high-friction material. To assemble insertion system 100, as shown in FIG. 4A, the obturator 104 is fully inserted (fully closed position) into insertion housing 102, and ICM 108 is inserted into insertion housing 102. Insertion system 100 may be packaged and distributed to clinicians in a fully assembled (i.e., pre-loaded) configuration, as shown in FIG. 4A. Alternatively, the components of insertion system 100 may be assembled on-site where the implantation procedure is to take place. Once ICM 108 is inserted into receptacle 154, detents 155 (also referred to as projections) prevent ICM 108 from falling out of the receptacle 154 into ambient environment. For example, the detents 155 may engage ICM 108 in a snap-fit engagement to maintain ICM 108 in receptacle 154. As shown in FIG. 4A, when ICM 108 is inserted into receptacle 154, the obturator 104 is already inserted into the passage 107 and traverses the receptacle section 111. Accordingly, obturator 104 initially prevents the ICM 108 from entering the portion of the passage 107 within the receptacle section 111. Optionally, the ICM may be pre-installed into the insertion housing 102 before the implant procedure begins. A method of implanting ICM 108 using insertion system 100 will now be described with respect to FIGS. 4A-4C. An incision (e.g., a 6-12 millimeter (mm) incision) is made in the patient using, for example, a surgical scalpel. The obturator 104 and insertion housing 102 are initially positioned, relative to one another, in a blunt dissection state 402 (as shown in FIG. 4A). When in the blunt dissection state 408, the distal end 166 of the obturator 104 is extended to project from the distal end 112 of the insertion housing 102. The distal end 166 of the obturator 104 is inserted through the incision (denoted by dashed line 167) into the patient's tissue. The tapered shape of distal end 166 provides a relatively small spear-shaped entry point into the tissue. To push the channel forming section 172 of the obturator 104 further into the tissue, the clinician may rotate, torque, and maneuver the insertion housing 102. The clinician continues to apply pressure until the distal end 112 of the insertion housing 102 is inserted through the incision 167 into the patient's tissue (FIG. 4B). The tapered shape of distal end 112 also provides a relatively small spear-shaped entry point into the tissue for the insertion housing 102.

As the channel forming section 172 (and optionally, the blunt dissection barrel 113) is inserted to a desired depth, the user applies a force to the handle 106 of the obturator 104 to maintain the distal end 166 of the obturator 104 projected from the distal end 112 of the insertion housing 102.

Alternatively, the blunt dissection barrel 113 may be initially inserted into the patient's tissue, with the obturator 104 partially retracted, that may also be referred to as the blunt dissection state. As a further option, the obturator 104 may be retracted even further from the insertion housing 102, such as to the positions shown in either of FIG. 4C, or any intermediate position there between. When the obturator 104 begins in a retracted position (during the blunt dissection state), once the blunt dissection barrel 113 is inserted below the tissue, the distal end 166 is then extended until projecting from the blunt dissection barrel 113 by a desired amount, such as illustrated in FIG. 4A. The obturator 104 moves along a range of motion corresponding to an ICM pocket formation path until reaching a fully extended position corresponding to an ICM pocket formation state 402. The obturator 104 moves along the pocket formation path until the channel forming section 172 extends a predetermined distance from the distal end 112 of the insertion housing 102 as shown in FIG. 4A. The predetermined distance is defined by the motion limiter 190 when moved along the first range to the first position (FIG. 2C).

The channel forming section 172 is shaped and dimensioned to form a channel or pocket under the patient's tissue to receive the ICM 108. Once the pocket is formed, the user withdraws the obturator 104, while holding the insertion housing 102 in the initial position with the blunt dissection barrel 113 located under the patient tissue. The obturator 104 is pulled back, relative to the insertion housing 102.

FIG. 4B illustrates an ICM loading state 404, at which the obturator 104 is substantially withdrawn from the insertion housing 102. When in the ICM loading state 404, the channel forming section 172 of the obturator 104 is withdrawn from the proximal section 115 of the insertion housing 102, until the distal end 166 is positioned outside or behind the receptacle section 111. Once the distal end 166 clears the receptacle section 111 of the passage 107, the ICM 108 drops into the passage 107. The ICM 108 may drop into the passage 107 due to gravity. Optionally, the user may apply a slight force with a thumb or finger to the ICM 108 to ensure proper loading. The ICM 108 resides within the passage 107 when in the ICM loading state 404, and is thus ready to be implanted.

FIG. 4C illustrates an ICM final implant state 406. The obturator 104 is moved along an ICM final implant path until reaching the ICM final implant state 406, at which the obturator 104 is inserted by a predetermined distance into the insertion housing 102. When in the ICM final implant state 406, the distal end 166 of the obturator 104 coincides with the distal end 112 of the blunt dissection barrel 113. When in the ICM final implant state 406, the distal end 166 of the obturator 104 has forced the ICM 108 to discharge from the blunt dissection barrel 113 and reside within the pocket under the patient's tissue. In the example of FIG. 4C, a dashed line 167 indicates a point of incision where everything to the left of the dashed line 167 is in the tissue past the point of incision. The ICM is 108 implanted a desired distance, for example governed by length 158 (FIG. 1A), beyond the incision line.

To implant the ICM 108, using obturator handle 106, the clinician pushes the obturator 104 further into insertion housing 102 such that the obturator 104 moves relative to insertion housing 102. As shown in FIGS. 4A-4C, pushing the obturator 104 in turn pushes ICM 108 through insertion housing 102. The clinician continues to push the obturator 104 until the latch arm 192 moves along the second range to the second position and prevents further movement, thereby defining an end of the ICM final implant path. For example, as explained in connection with FIGS. 3A-3B, the latch arm 192 engages the ledge 195 to define a stopping point for the insertion of the obturator 104. In the illustrated embodiment, the portion of the length of the obturator 104 beyond the latch arm 192 is approximately equal to the length of insertion housing 102. Accordingly, as shown in FIG. 4C, when the latch arm 192 contacts the ledge 195, the ICM 108 is fully deployed (i.e., ICM 108 is positioned entirely outside of insertion housing 102). This enables the clinician to confirm that ICM 108 is fully deployed in the tissue, even though the clinician will generally be unable to visually confirm the position of ICM 108. After ICM 108 is deployed, the clinician removes insertion housing 102 from the incision and closes the incision using known closure techniques (e.g., adhesive strips, sutures, etc.).

Optionally, a knob may be provided on the handle 106 of the obturator 104. The knob may be rounded informed of a somewhat flexible material, such as silicone, to be comfortable in the palm of a user when applying force to the obturator 104.

Figure 5A:
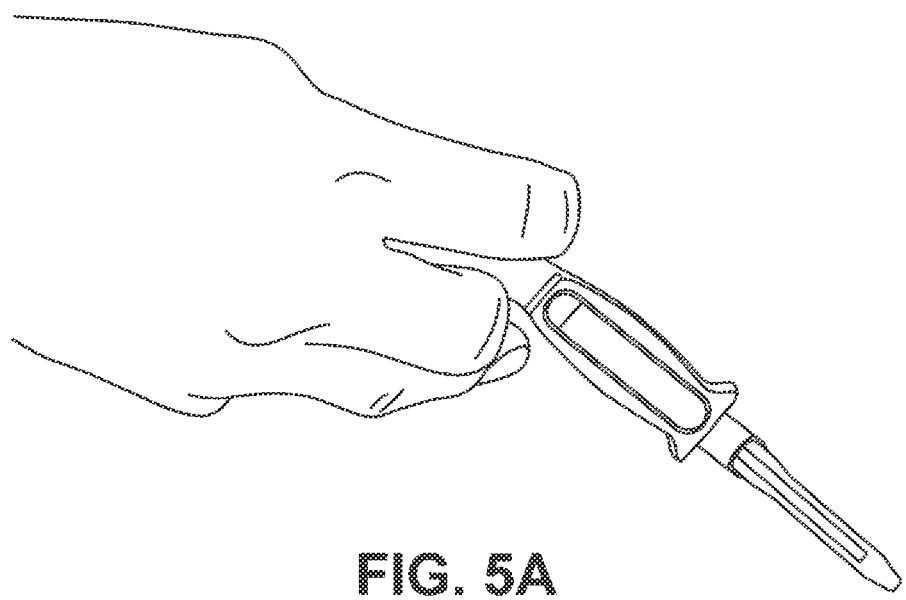
FIG. 5A illustrates a manner in which the system of FIGS. 4A-4C may be held in the user's hand in accordance with embodiments herein.
Figure 5B:
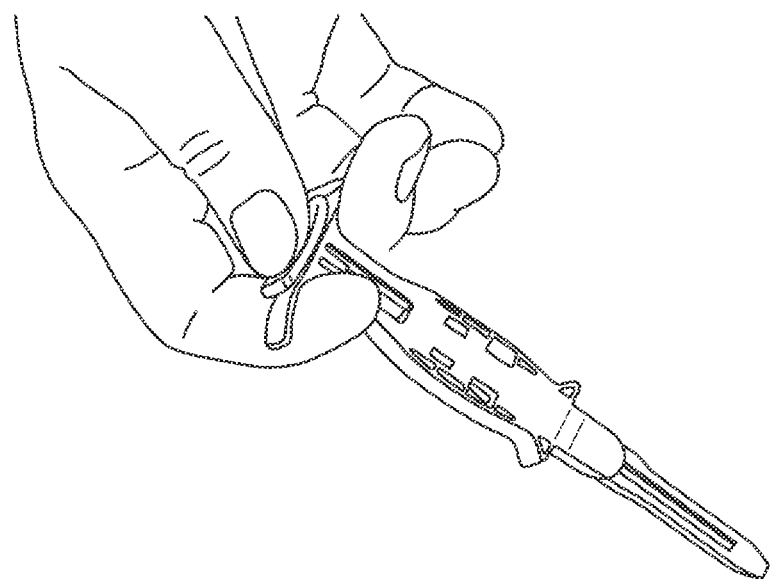
FIG. 5B illustrates a manner in which the system of FIGS. 4A-4C may be held in the user's hand in accordance with embodiments herein.

FIGS. 5A and 5B illustrate a manner in which the system 100 of FIGS. 1 and 2 may be held in the user's hand. An index finger and middle finger the user's hand are positioned over the wings at the proximal end of the insertion housing, while the user's thumb presses on the handle of the obturator, similar to the operation used with a syringe.

Optionally, an indicator may be provided to facilitate aligning the insertion housing during an implantation procedure, as described herein. The indicator may be a colored (e.g., red) band formed on the outside of blunt dissection barrel. Alternatively, the indicator may be any indicia and/or feature that enables the indicator to function as described herein.

The ICM insertion systems and methods described herein facilitate relatively straightforward implantation of an ICM into a patient. Specifically, the systems and methods described herein facilitate keeping an incision propped open, maneuvering an insertion housing within tissue, guiding placement of the ICM, deploying the ICM such that there is little to no space between the ICM and the surrounding tissue, and removing the insertion housing after deployment of the ICM is complete.

Implant Location Mapping

Next, embodiments are described herein that may be utilized in connection with an implant location mapping operation to determine whether an ICM candidate location (e.g., region where the ICM is planned to be implanted) and orientation (e.g., vertical, diagonal, horizontal) would yield physiologic signals, from which one or more characteristics of interest can be reliably analyzed. For example, when implanting an ICM to monitor cardiac activity, the characteristic of interest may represent the peak of the R-wave.

During the implant location mapping operation, a medical instrument is used to record cardiac signals. The cardiac signals are then analyzed to identify R-waves, such as within an EKG signal. The R-waves are compared to one or more signal criteria, such as comparing a peak of the R-wave to an R-wave threshold. When the measured cardiac signals yield R-waves having sufficient amplitude, the physician can determine that, if the ICM is implanted in the present candidate location at the present orientation, the ICM would yield satisfactory cardiac signals. Alternatively, if the cardiac signals do not exhibit an R-wave having satisfactory characteristics (e.g., amplitude below a threshold), the physician may determine that the present ICM candidate location and/or orientation would not yield sufficient cardiac signals. Accordingly, the physician may choose to adjust the position of the medical instrument to test alternative ICM candidate locations. The adjustment may merely involve turning the medical instrument along a longitudinal axis. Additionally or alternatively, the adjustment may involve slightly or substantially reorienting an angular position of the medical instrument. Additionally or alternatively, the adjustment may involve testing an entirely separate ICM candidate location.

Figure 6A:
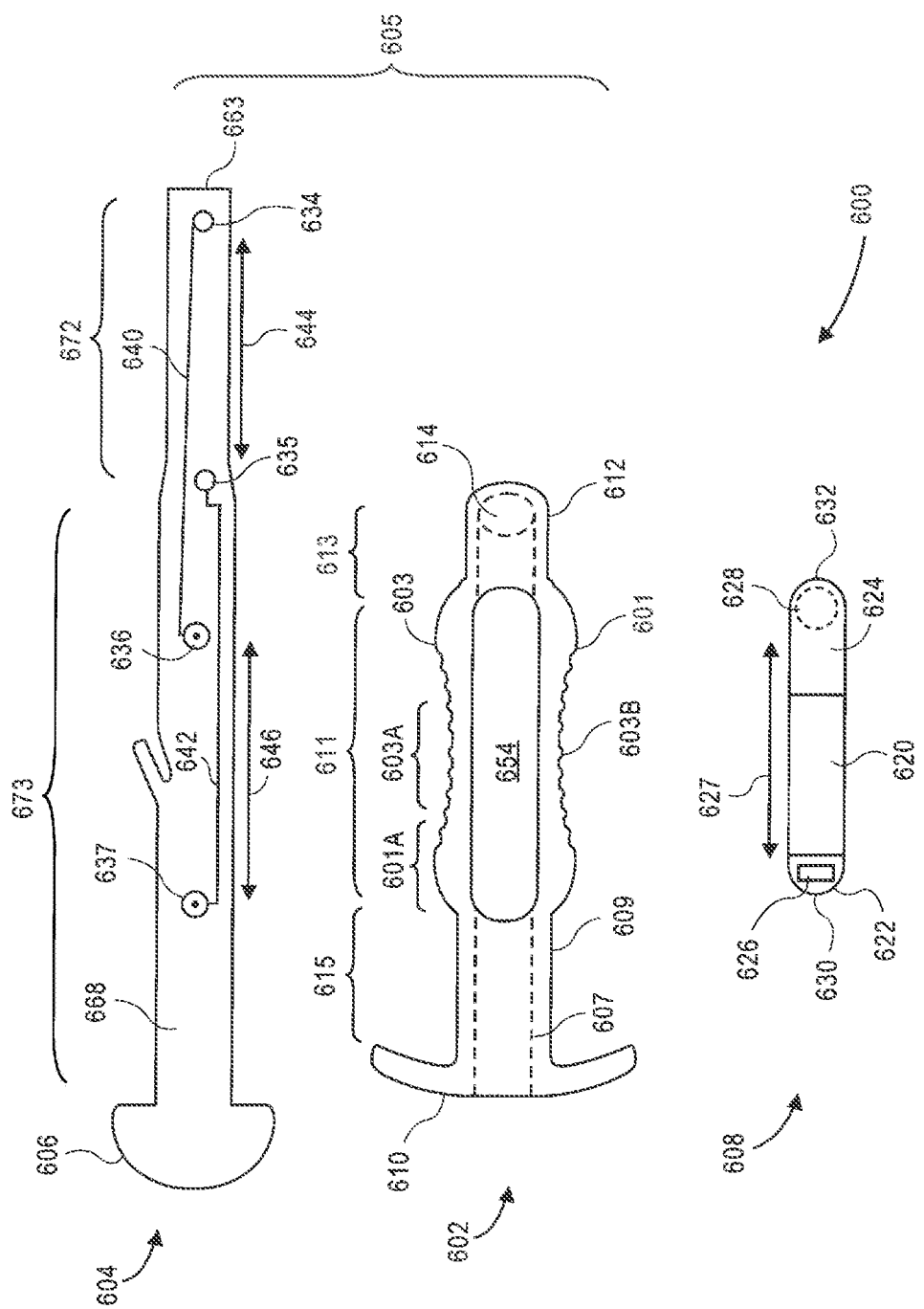
FIG. 6A illustrates an insertion system formed in accordance with an alternative embodiment and utilized to perform implant location mapping in accordance with embodiments herein.
Figure 6B:
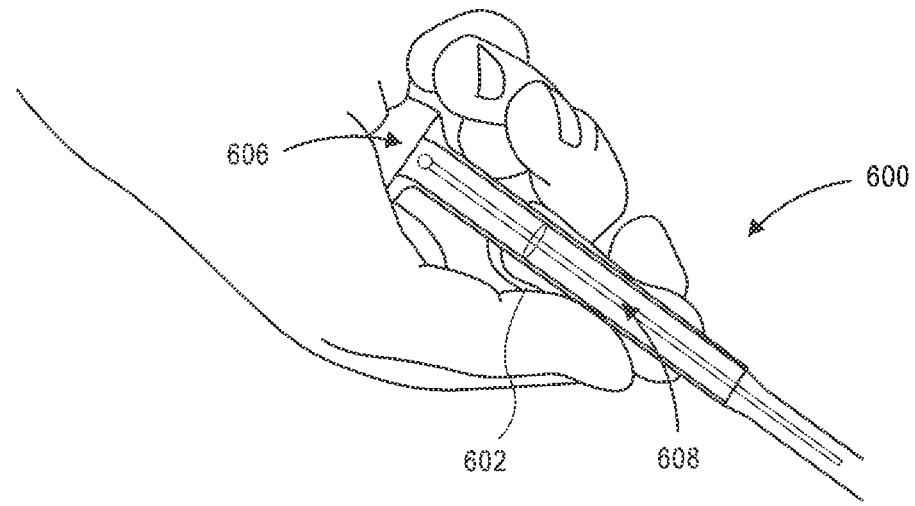
FIG. 6B illustrates a manner in which the system of FIG. 6A may be held in the user's hand in accordance with embodiments herein.
Figure 6C:
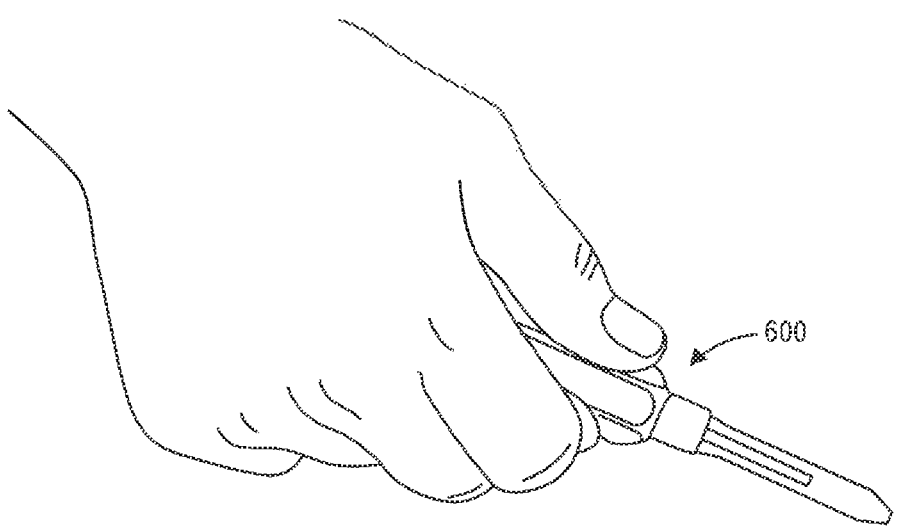
FIG. 6C illustrates a manner in which the system of FIG. 6A may be held in the user's hand in accordance with embodiments herein.

FIG. 6A illustrates an insertion system 600 formed in accordance with an alternative embodiment and utilized to perform implant location mapping. The insertion system 600 includes an insertion housing 602, an obturator 604 and an ICM 608. The insertion housing 602 and obturator 604 represent a medical instrument utilized in connection with performing implant location mapping and may include some or all of the features discussed in connection with FIGS. 1-5. In the example of FIG. 6A-6C, the insertion housing 602 is provided with a different shape than the insertion housing 102 of FIGS. 1A and 1B. Optionally, the insertion housing 102 may be utilized with implant location mapping. Further, the insertion housing 602 may be utilized in connection with the embodiments of FIGS. 1A and 1B without adding the implant location mapping features. The insertion housing 602 includes a barrel 609 with a passage 607 extending between a first/proximal end 610 and a second/distal end 612. The second end 612 includes an opening 614, from which the distal portion of the obturator 604 and the ICM 608 extend at various states of the implant process. The barrel 609 includes a central reception section 611, a blunt dissection barrel 613 and a proximal section 615, similar to the configuration described in connection with FIGS. 1-5. The reception section 611 includes a reception cavity 654 that is configured to receive the ICM 608 during an implant process.

The insertion housing 602 includes lateral surfaces 601 and 603 that are arranged in a concave manner to form an hourglass shape with a narrow portion 603A located between opposed wider portions 601A. The lateral surfaces 601 and 603 include ribs 603B (also referred to as vertical knurls). The concave arrangement of the lateral surface 601 and 603 and the ribs 603B improve grip integrity between the thumb and index finger when grasped by the user.

The obturator 604 includes a handle 606 that is connected to one end of a shaft 668. The shaft 668 extends from the handle 606 to a distal end 666. The shaft 668 includes a channel forming section 672 that is configured to form an ICM pocket under the tissue during the implant process. The channel forming section 672 represents one example of a channel preparation element that is configured to be inserted subcutaneously. As explained herein, additional or alternative channel preparation elements may be utilized during the mapping operation.

In the illustrated embodiments, the channel forming section 672 has a smaller cross-section than a remainder of the shaft 668. Optionally, the channel forming section 672 may have the same cross-sectional dimensions as a remainder of the shaft 668. Alternatively, the shaft 668 may have smaller cross-sectional dimensions and/or a different cross-sectional shape than the dimensions and shape of the channel forming section 672.

The ICM 608 includes a housing 620 that is attached at one end to a header 622, and at an opposite end to a battery 624. The header 622 includes at least one electrode 626 that is provided along one side thereof. An exterior shell enclosing the battery 624 is utilized as an electrode 628 generally denoted by dashed lines; although, it is recognized that a larger portion of the shell of the battery 624 may be used as the electrode 628. The electrodes 626 and 628 are generally separated from one another by an electrode spacing 627. The electrodes 626, 628 may also be referred to as ICM electrodes. The ICM electrodes 626 and 628 are located on a common side of the ICM 608. It should be recognized that the entire shell of the battery 624 may be utilized as an electrode, and thus, the electrode 628 may substantially surround the end of the ICM 608 in the region corresponding to the battery 624. Optionally, subsections of the shell for the battery 624 may be covered with insulation, while other subsections of the shell are exposed to define discrete regions for the electrode 628. The electrode(s) 626 is provided along one or both sides of the header 622.

The header 622, housing 620 and battery 624 cooperate to define generally an overall rectangular shape with rounded edges between the sides and with rounded ends 630 and 632 (although other shapes may be used). During operation, the ICM 608 performs sensing operations utilizing the electrodes 626 and 628, in order to sense and record physiologic signals. Various types of physiologic signals may be collected, such as cardiac signals, respiratory signals, impedance signals, neurological signals and the like, depending upon the location in which the ICM 608 is positioned and the nature of the sensing circuitry within the ICM 608.

In connection with a mapping operation, the obturator 604 includes electrodes 634, 635 arranged along section 672 of the shaft 668. The electrodes 634, 635 are also referred to as instrument electrodes in order to be distinguished from the ICM electrodes 626, 628. The obturator 604 also includes contacts 636 and 637 that are positioned along a main body section 673 of the obturator 604.

The instrument electrode 634 and contact 636 are electrically coupled to one another through a conductor 640, while the electrode 635 and contact 637 are connected to one another through a conductor 642. The conductors extend along or within the shaft 668. The electrodes 634 and 635 are separated by an electrode to electrode spacing 644 that generally corresponds to the electrode spacing 627 between the ICM electrodes 626, 628. The instrument electrodes 634, 635 are separated by the electrode spacing 644 in order that the system can perform implant location mapping during the implant process based on an electrode spacing that conforms to the electrode spacing 627 of the ICM, but prior to implanting the ICM.

The contacts 636, 637 are separated from one another along the shaft 668 by an electrode to electrode spacing 646 that also corresponds to the electrode spacing 627, in order that, when the ICM 608 is inserted into the receptacle 654, the contacts 637, 636 physically and electrically engage the ICM electrodes 626, 628.

Optionally, the electrode spacing 646 between the contacts 636, 637 may be adjusted so long as the contacts 636,637 align with the ICM electrodes 626, 628. Optionally, the contacts 636, 637 may be provided on one or more interior surfaces of the receptacle 654 in the insertion housing 602. To do so, conductors are provided to couple the instrument electrodes 634, 635 from the obturator 604 to contacts on the insertion housing 602.

The physiologic signals collected at the instrument electrodes 634, 635 may be conveyed to the ICM 608 and/or an external monitoring device in accordance with alternative embodiments herein. In the example of FIG. 6, the physiologic signals sensed at the instrument electrodes 634, 635 are conveyed to the ICM 608 through the contacts 636, 637.

FIGS. 6B and 6C illustrate a manner in which the system 600 of FIG. 6A may be held in the user's hand. A thumb and forefinger of the user's hand are positioned within the narrow portions along the lateral surfaces. The obturator handle 606 is held in a palm of the user's hand. The rounded end of the obturator handle 606 is configured to fit comfortably in the palm of the hand and allow the user firm control of the distal end of the obturator during the blunt dissection process when it is necessary to open tissue under the skin to make a channel for the ICM.

Figure 7:
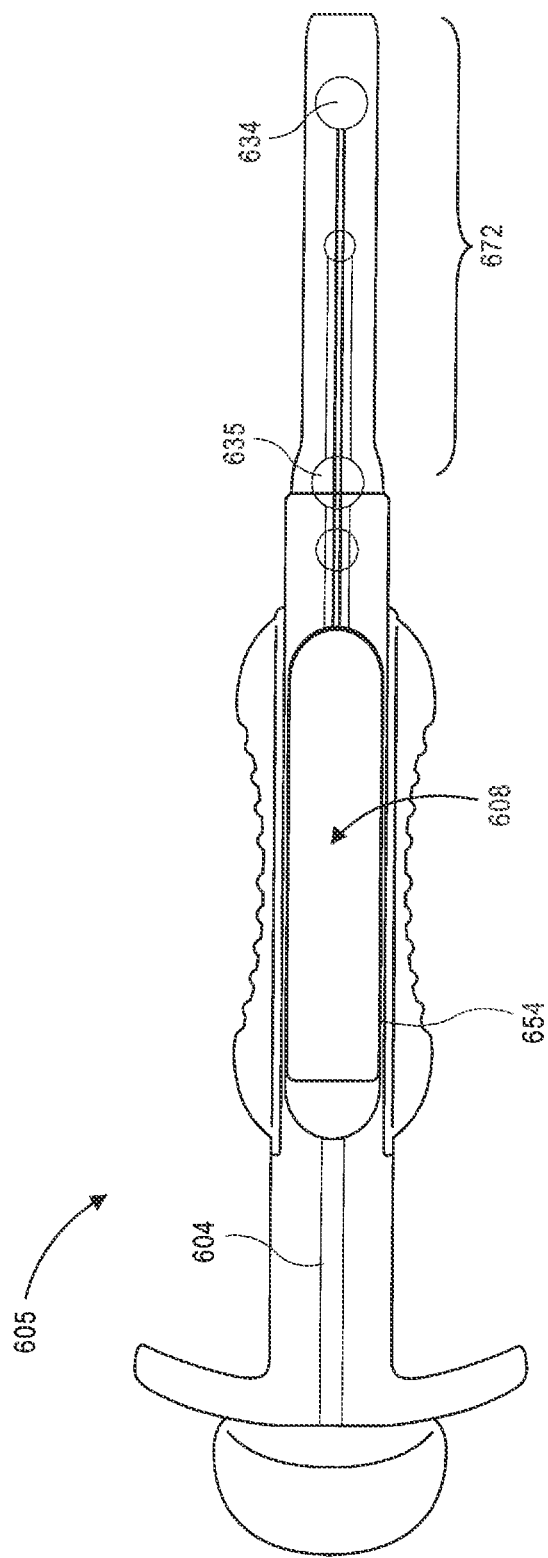
FIG. 7 illustrates the medical instrument, with the ICM installed into the receptacle in accordance with embodiments herein.

FIG. 7 illustrates the medical instrument 605, with the ICM 608 inserted into the receptacle 654. The ICM 608 is positioned such that the electrodes 626 and 628 face downward toward the bottom of the receptacle 654 in order to engage the contacts 637, 636 (FIG. 6) on the obturator 604. Once the channel forming section 672 is inserted subcutaneously into an ICM candidate location, the instrument electrodes 634, 635 convey physiologic signals to the ICM 608. The ICM 608 may wireless convey the physiologic signals to an external device.

The ICM 608 and/or external device may analyze the physiologic signals, such as i) to identify whether the amplitude of the P-wave satisfies a P-wave threshold, ii) to identify whether the amplitude of the R-wave satisfies a R-wave threshold or iii) to analyze some other characteristic of interest. When the ICM 608 performs the analysis and the characteristic of interest satisfies the corresponding signal criteria, the ICM 608 may convey an indication to an external monitor (e.g., via a Bluetooth or other wireless communications link) that the present candidate location and orientation are satisfactory. Alternatively, the ICM 608 may convey an indication to the external monitor that the present candidate location and orientation are not satisfactory. The process for mapping candidate implant locations is described below in more detail in connection with FIG. 10.

Figure 8:
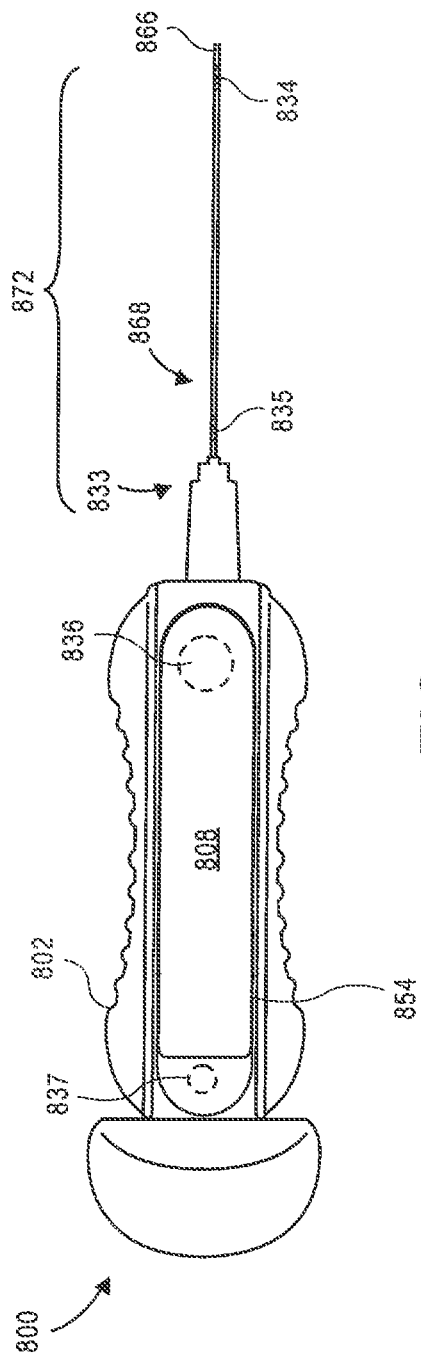
FIG. 8 illustrates a medical instrument formed in accordance with an alternative embodiment for mapping.

FIG. 8 illustrates a medical instrument 800 formed in accordance with an alternative embodiment for mapping. The medical instrument 800 includes an ICM 808 that is inserted into a receptacle 854 formed within a probe body 802. The probe body 802 is shaped similarly to an insertion housing (as described above in connection with FIGS. 1-6). Optionally, the probe housing 802 may include alternative shapes and designs. The probe housing 802 is attached to a proximal end of a needle 868. The needle 868 may represent a lumen built-in to the obturator. The needle 868 includes instrument electrodes 834 and 835 provided at the distal end 866 and the proximal end 833. The needle 868 represents another type of channel preparation element 872. The needle 868 is inserted at an ICM candidate location and with a desired orientation.

The electrodes 834 and 835 are coupled via conductors with contacts 836 and 837 (denoted in hidden line) that are provided in a bottom of the receptacle 854 in the probe body 802. The contacts 836, 837 are positioned to align with electrodes on the ICM 808 (similar to the embodiments described above in connection with FIGS. 6 and 7).

During operation, the user inserts the needle 868 to the candidate location and waits for collection of physiologic signals, analysis of characteristics of interest therein and a determination of whether the candidate implant location and orientation would result in physiologic signals of sufficient amplitude. The indication of whether the candidate implant location is satisfactory may be provided by an external device. In response thereto, the physician continues the implant process at the present candidate implant location and orientation, or alternatively removes the needle 868 and inserts the needle at a new candidate implant location and/or orientation.

Figure 9:
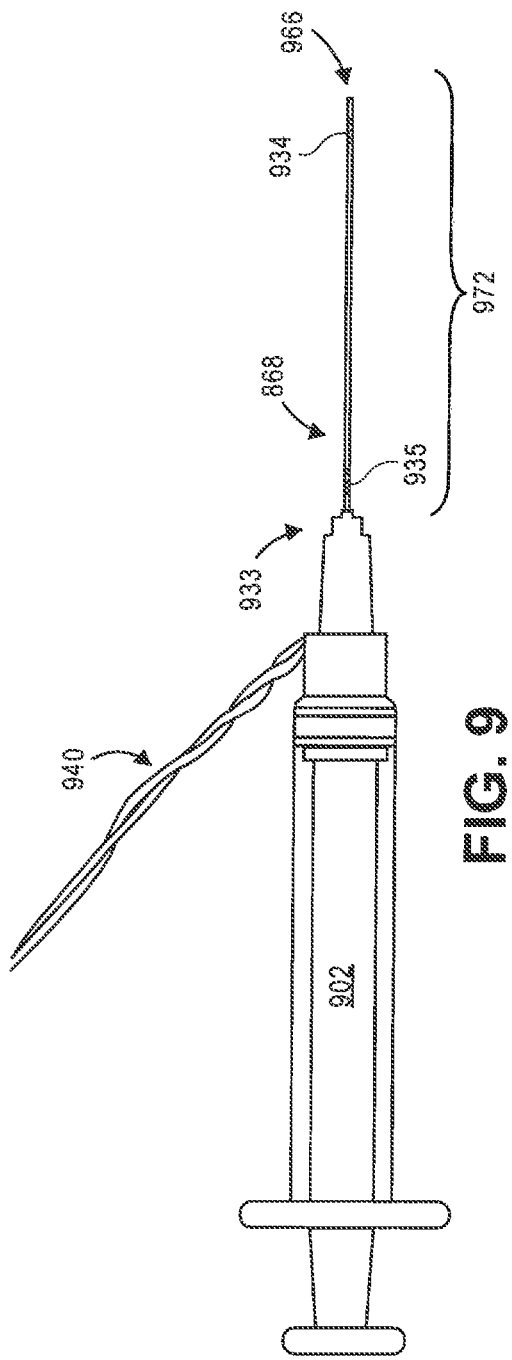
FIG. 9 illustrates a medical instrument formed in accordance with an alternative embodiment for mapping.

FIG. 9 illustrates a medical instrument 900 formed in accordance with an alternative embodiment for mapping. The medical instrument 900 includes a syringe 902. For example, the syringe may be utilized to inject lidocaine or another similar substance, such as in connection with numbing a candidate implant site. The syringe 902 is attached to a proximal end of a needle 968. The needle 968 includes instrument electrodes 934 and 935 provided at the distal end 966 and the proximal end 933. The needle 968 represents another type of channel preparation element 972. The needle 968 is inserted at a candidate location and at a desired orientation.

The electrodes 934 and 935 are coupled via conductors 940 to an external monitoring device. Optionally, the conductors 940 may be coupled to an ICM receptacle (e.g., similar to the receptacles illustrated in FIGS. 1-8). The external monitoring device and/or ICM may collect physiologic signals and perform the analysis described herein to determine whether the location and orientation of the needle 968 represents an acceptable implant location. The needle 968 represents another type of channel preparation element 972.

During operation, the user inserts the needle 968 to the candidate implant location and waits for the ICM 808 and/or external device to collect physiologic signals, analyze characteristics of interest therein and determine whether the candidate implant location and orientation would result in physiologic signals of sufficient amplitude. In response thereto, the physician continues the implant process at the present candidate implant location and orientation, or alternatively removes the needle 968 and inserts the needle at a new candidate location and/or orientation.

Figure 10:
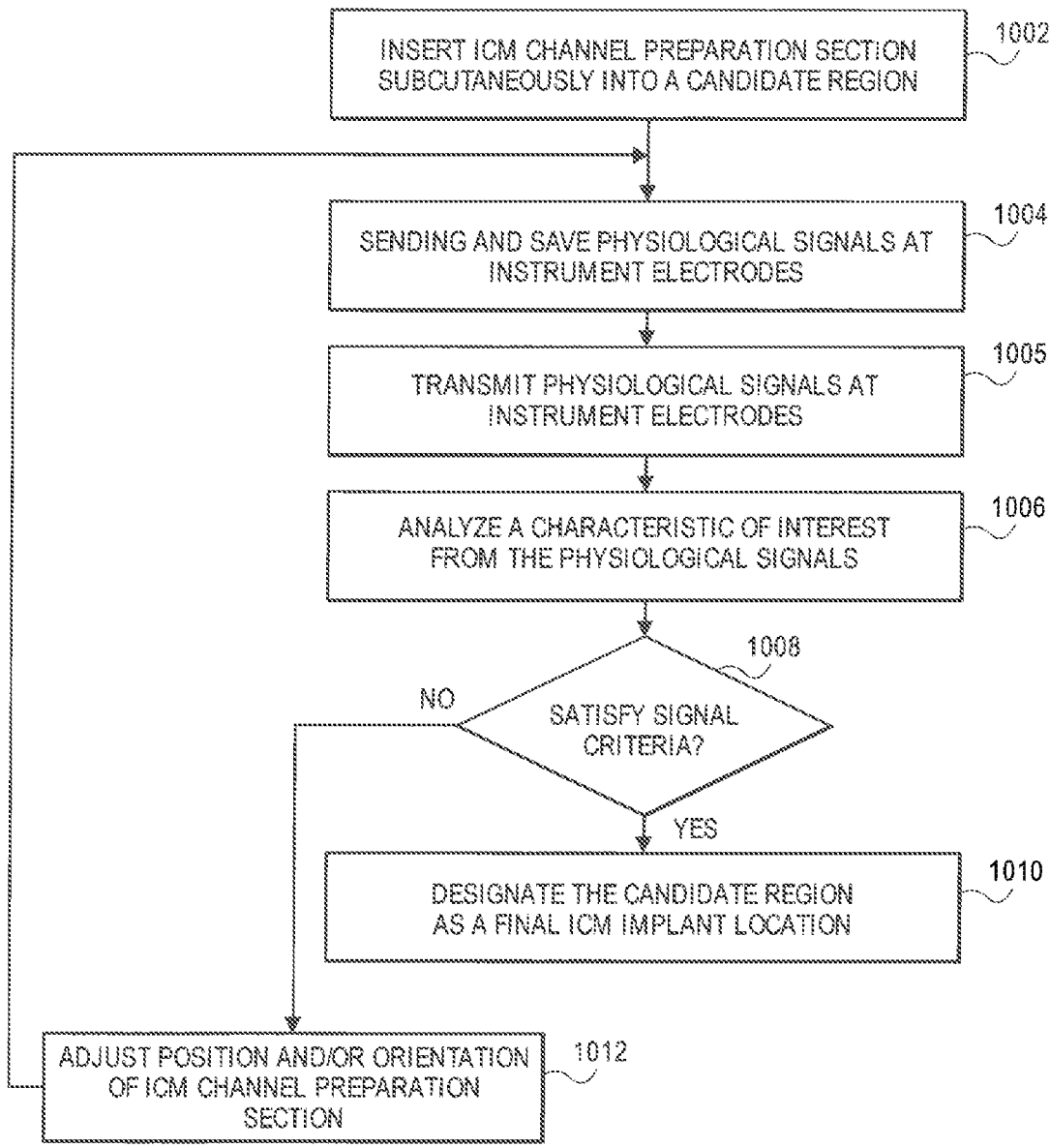
FIG. 10 illustrates a method for mapping an implant location and orientation for an ICM device in accordance with embodiments herein.

FIG. 10 illustrates a method for mapping an implant location for an ICM device in accordance with embodiments herein. At 1002, a channel preparation element of a medical instrument is inserted subcutaneously at an ICM candidate location. The channel preparation element may differ based upon the stage in the implant process or the nature of the system. For example, at 1002, a syringe with a needle (FIG. 9) may be inserted to introduce lidocaine or another numbing agent. Additionally or alternatively, a needle may be inserted that is provided on an instrument similar to the instrument illustrated in FIG. 8. Additionally or alternatively, the channel forming section 672 of an obturator 604 (FIG. 6) may be inserted.

At 1004, physiologic signals are sensed at first and second instrument electrodes located along the channel preparation element. The sensed physiologic signals may be conveyed and recorded at an ICM and/or and external monitoring device. For example, as illustrated in connection with FIGS. 6-8, the physiologic signals sensed at the instrument electrodes are conveyed to and recorded by an ICM that is directly connected to the medical instrument. Additionally or alternatively, the physiologic signals, sensed at the instrument electrodes are conveyed through a wired connection to and recorded by an external monitoring device.

As noted herein, various types of physiologic signals may be sensed and collected. For example, the physiologic signals may represent cardiac signals, respiratory signals, impedance signals, neurological signals, brain waves and the like. While the illustrated embodiments utilize two instrument electrodes, it is recognized that more instrument electrodes may be utilized. For example more than two instrument electrodes may be provided along the shaft 668 of the obturator 604. When more than two electrodes are provided on the obturator 604, all or a subset of the electrodes may be utilized during any individual sensing operation. As one example, physiologic signals may be sensed and collected between different combinations of instrument electrodes at 1004, where the different combinations of electrodes represent different candidate locations. For example, when a needle is inserted with a series of electrodes thereon, the needle may be longer than the length of an ICM. Different combinations of the electrodes along the needle may be used to collect physiologic signals.

An optional operation is provided at 1005. At 1005, when the physiologic signals are conveyed from the instrument electrodes to the ICM, the ICM may wirelessly transmit the physiologic signals to an external device (e.g., through a Bluetooth transmitter or other wireless protocol). For example, the external device may represent a cell phone, tablet computer, laptop computer, home medical monitoring device, physician-patient monitor and the like. The external device may then analyze the physiologic signals as described hereafter. Optionally, the ICM need not transmit the physiologic signals to any external device, but instead, the ICM may perform the analysis described hereafter and merely provide an indication regarding the results of the analysis to the external device.

At 1006, one or more processors (within the ICM and/or an external device) are utilized to analyze a characteristic of interest from the physiologic signals relative to the signal criteria. As one example, when the physiologic signals represent cardiac signals, the characteristic of interest may represent one or more features of the cardiac cycle (e.g., the peak of the R-wave, peak of a P-wave, etc.). The analysis may involve comparing the characteristic of interest to one or more signal criteria (e.g., one or more thresholds). As one example, each P-wave may be compared to a P-wave threshold where the threshold defines the minimum acceptable amplitude for the P-wave to justify the candidate implant location and orientation. As another example, the R-waves may be compared to an R-wave threshold for a similar determination. Additionally or alternatively, other aspects of the P-wave and/or R-wave may be compared with thresholds.

As another example, when the physiologic signal represents a neurological signal or brainwave, the characteristic of interest may represent an amplitude or overall activity of evoked potentials from nerve fibers or brain waves within a select frequency range.

Optionally, the analysis at 1006 may involve combining multiple physiologic signals such as to develop an ensemble average over multiple cardiac cycles. The ensemble average may then be compared with one or more thresholds.

At 1008, the characteristic of interest is compared to the signal criteria to determine whether the signal criteria are satisfied. When the signal criteria are satisfied, flow moves to 1010. At 1010, the ICM candidate location is designated as a final ICM implant location.

Returning to 1008, when the signal criteria are not satisfied, flow moves to 1012. At 1012, the user is informed that the ICM candidate location has not provided a physiologic signal that satisfies the signal criteria. Accordingly, the user adjusts a position and/or orientation of the channel preparation element of the medical instrument. For example, the user may entirely withdraw the medical instrument from the subcutaneous position and reinsert the channel preparation element. Alternatively, the user may shift an orientation of the medical instrument utilizing a slight prying force and/or by rotating the medical instrument about a longitudinal axis thereof. As another example, the user may partially withdraw the medical instrument to change the insertion angle and reinsert the channel preparation element along a new trajectory. The operations of FIG. 10 may be repeated until the signal criteria are satisfied for the characteristic of interest.

The indication regarding whether the characteristic of interest satisfies the signal criteria may be provided in various manners. For example, the external device may provide a visual and/or audible indication to the user (e.g., yes, no, green light, red light, yellow light, percentage compliance). Additionally or alternatively, the external device may provide the raw results of the analysis without a direction as to whether the present implant location is satisfactory. For example, the external device may indicate the characteristic of interest such as the signal strength of the physiologic signal, the number of P-waves and/or R-waves detected, the amplitudes of the P-waves and/or R-waves detected, the number of P-waves and/or R-waves that exceed a threshold, an average amplitude difference between the measured P-waves and a P-wave minimum amplitude threshold, an average amplitude difference between the measured R-waves and an R-wave minimum amplitude threshold and the like. Additional or alternative indications may be provided to inform the user regarding the nature of the characteristic of interest from the physiologic signal and additional information regarding whether the present candidate implant location is satisfactory.

Optionally, the external device may provide the foregoing information regarding the results of the analysis verbally (e.g., audibly stating a size of a QRS complex as measured in millivolts). Additionally or alternatively, the external device may audibly inform the user each time a P-wave is discerned, the number of P-waves discerned over a period of time and/or number of cardiac cycles, and the like.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An insertion system comprising:
    an obturator;
    an implantable cardiac monitor (ICM);
    an insertion housing comprising:
        a passage extending from a first end of the insertion housing through a receptacle section of the insertion housing to a second end of the insertion housing, the passage configured to receive the obturator; and a receptacle cavity provided in the receptacle section and in communication with the passage and an external environment, the receptacle cavity configured to hold the ICM while the obturator is located in the passage and while the obturator is moved within the passage from a position proximal to the receptacle cavity to a position distal to the receptacle cavity within the insertion housing;

the obturator having a channel forming section at a distal end thereof; and a motion limiter provided on at least one of the obturator and the insertion housing.

2. The system of claim 1, wherein the ICM is configured to move from the receptacle cavity into the passage when the obturator is withdrawn from a portion of the passage proximate the receptacle cavity and the obturator is configured to push the ICM along the passage when the operator moves along an ICM final implant path and the motion limiter defines an end of the ICM final implant path, the distal end of the obturator being positioned substantially flush with the second end of the insertion housing when reaching the end of the ICM final implant path.

3. The system of claim 1, wherein the obturator is configured to move along a pocket formation path, the motion limiter includes a latch arm located along a side of a shaft of the obturator and at least one recessed region in the passage, the latch arm extending laterally outward from the side into the at least one recessed region when the obturator moves to an end of the pocket formation path and when the obturator moves to an end of the ICM final implant path.

4. The system of claim 1, wherein the motion limiter includes at least one latch and at least one recessed region provided on the obturator and insertion housing.

5. The system of claim 1, wherein the channel forming section has a cross-section and is sized and dimensioned similar to a cross-section, size and dimension of the ICM.

6. The system of claim 5, wherein the channel forming section of the obturator is configured to be utilized during a blunt dissection stabbing action to form an initial channel under patient tissue.

7. The system of claim 1, wherein the insertion housing includes a blunt dissection barrel provided at the second end, the blunt dissection barrel is configured to be utilized during a blunt dissection stabbing action to form an initial channel under patient tissue, the blunt dissection barrel having a length that is shorter than a length of the ICM.

8. The system of claim 7, wherein a length of the blunt dissection barrel is no more than one third of a length of the ICM.

9. A method for operating an insertion system, the method comprising:

inserting an obturator into a passage in an insertion housing such that the obturator extends from a first end of the insertion housing through a second end of the insertion housing;

inserting an implantable cardiac monitor (ICM) into a receptacle of the insertion housing, wherein the receptacle is in communication with the tube of the insertion housing, the receptacle configured to hold the ICM while the obturator is located in the passage and while the obturator is moved within the passage from a position proximal to the receptacle to a position distal to the receptacle within the insertion housing;

the obturator configured to move along a first range until the channel forming section extends a predetermined distance from the second end of the insertion housing, the predetermined distance being defined by a motion limiter;

the obturator configured to move along a second range in which the channel forming section forces the ICM from the second end of the insertion housing.

10. The method of claim 9, further comprising initially positioning the obturator and insertion housing in a blunt dissection state, when the obturator and a blunt dissection barrel at the second end of the insertion housing is inserted through an incision to a desired depth, moving along a range of motion corresponding to an ICM pocket formation path until reaching a fully inserted position corresponding to an ICM pocket formation state.

11. The method of claim 9, further comprising applying force to a handle of the obturator to maintain a channel forming section at the distal end of the obturator extended from the second end of the insertion housing to form an ICM pocket.

12. The method of claim 11, further comprising, once the ICM pocket is formed, pulling back on the obturator until the channel forming section of the obturator is positioned behind the receptacle of the insertion housing in order to permit the ICM to move into the passage.

13. The method of claim 12, further comprising applying force to the handle of the obturator to direct the distal end of the obturator to discharge the ICM from the second end of the insertion housing into the ICM pocket.

14. The method of claim 9, further comprising moving the obturator relative to the insertion housing until reaching the motion limiter, the motion limiter defining at least one of an end for a pocket forming state or an ICM final implant state for the obturator and insertion housing.

* * * * *